(12) United States Patent
Chait et al.

(10) Patent No.: US 7,968,299 B2
(45) Date of Patent: Jun. 28, 2011

(54) METHODS AND KITS FOR DISTINGUISHING BETWEEN SPECIFIC AND NON-SPECIFIC PROTEIN ASSOCIATIONS

(75) Inventors: Brian T. Chait, New York, NY (US); Alan J. Tackett, New York, NY (US); Jeffrey A. DeGrasse, New York, NY (US); Marlene Oeffinger, New York, NY (US); Michael P. Rout, New York, NY (US); Matthew D. Sekedat, New York, NY (US)

(73) Assignee: The Rockefeller University, New York, NY (US)

( * ) Notice: Subject to any disclaimer, the term of this patent is extended or adjusted under 35 U.S.C. 154(b) by 1250 days.

(21) Appl. No.: 11/508,736

(22) Filed: Aug. 21, 2006

(65) Prior Publication Data

US 2007/0077600 A1    Apr. 5, 2007

Related U.S. Application Data

(60) Provisional application No. 60/709,536, filed on Aug. 19, 2005.

(51) Int. Cl.
*G01N 33/53* (2006.01)
(52) U.S. Cl. .......................................... 435/7.1; 435/7.2
(58) Field of Classification Search .................... None
See application file for complete search history.

(56) References Cited

OTHER PUBLICATIONS

Schulze et al. "A Novel Proteomic Screen for Peptide-Protein Interactions." *The Journal of Biological Chemistry*, Mar. 12, 2004, 279(11):10756-10764.
Aebersold et al. "Mass Spectrometry-based Proteomics." *Nature*, Mar. 13, 2003, 422:198-207.
Ong et al. "Properties of $^{13}$C-Substituted Arginine in Stable Isotope Labeling by Amino Acids in Cell Culture (SILAC)," *Journal of Proteome Research*, (2003), 2:173-181 (Published on web Dec. 13, 2002).
Terpe, K., "Overview of Tag Protein Fusions: From Molecular and Biochemical Fundamentals to Commercial Systems." *Applied Microbiology and Biotechnology*, Jan. 2003, 60:523-533 (Published online Nov. 7, 2002).

*Primary Examiner* — Jacob Cheu
(74) *Attorney, Agent, or Firm* — Hoffman & Bacon, LLP

(57) ABSTRACT

The present invention is method of determining whether or not associations between a given protein and other proteins in a cell are specific. The method comprises (a) providing a first sample of the cells in which the given protein contains a tag, (b) providing a second sample of the same cells, wherein the given protein and the other proteins are metabolically labeled, and wherein neither the given protein nor the other proteins are tagged, (c) mixing and lysing the first cell sample and the second cell sample to provide a mixture of proteins, (d) binding the tag of the given protein to a substrate, (e) isolating proteins associated with the tagged given protein bound to the substrate, whereby the associated proteins comprise: (i) proteins specifically associated with the tagged given protein, (ii) proteins non-specifically associated with the tagged given protein, or (iii) a combination thereof, (f) determining whether each associated protein is unlabeled or a mixture of labeled and unlabeled proteins, wherein if the associated protein is not labeled, then that protein was specifically associated in the cell with the tagged given protein.

30 Claims, 4 Drawing Sheets

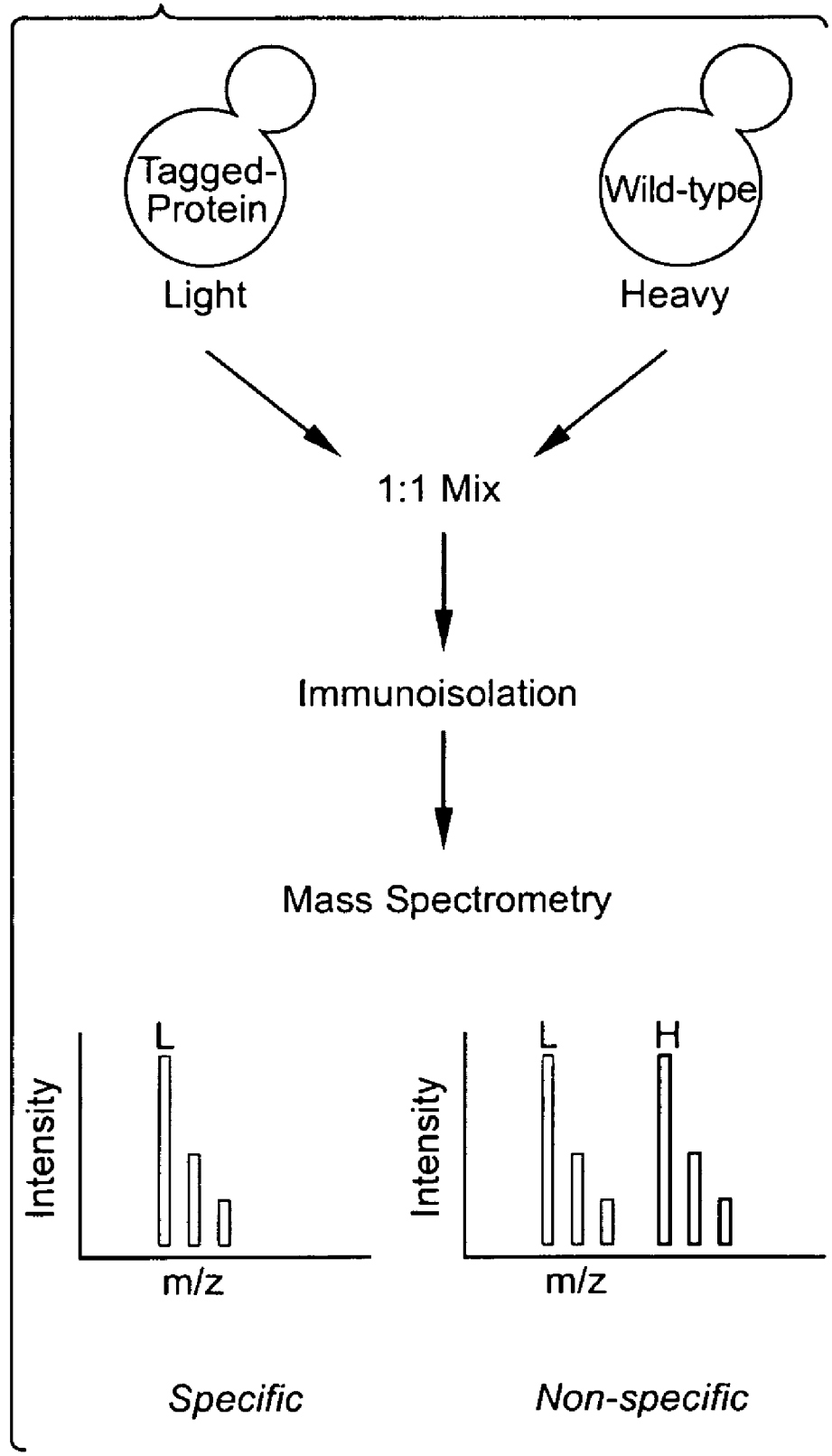

US 7,968,299 B2

METHODS AND KITS FOR DISTINGUISHING BETWEEN SPECIFIC AND NON-SPECIFIC PROTEIN ASSOCIATIONS

This application claims benefit of U.S. Provisional Application No. 60/709,536, filed Aug. 19, 2005, which is incorporated herein by reference.

This work was supported by grants from the NIH, grant numbers RR00862, GM062427, CA89810 and GM066496. The United States government has certain rights in this invention.

BACKGROUND OF THE INVENTION

Advances in rapid isolation techniques and mass spectrometric identification of protein complexes have produced a plethora of protein interaction data. (Gavin et al., *Nature* 2002, 415, 141-7; Ho et al., *Nature* 2002, 415, 180-3; Rout et al., *J Cell Biol* 2000, 148, 635-51; Archambault et al., *Cell* 2004, 14, 699-711; Sanders et al., *Cell Biol* 2002, 22, 4723-38.) Researchers are now faced with the challenge of determining which of these interactions are specific or non-specific to the complex under study. Protein complexes are now routinely immunoisolated from cell lysates via an affinity-tagged member of the complex(es). These technologies have become widely utilized in *S. cerevisiae* due to the relative ease of incorporating a genomic tag by homologous recombination, and also to the commercially available TAP-tag collection of dual affinity-tagged proteins. The immunoisolation technique is an exceptionally powerful method for rapidly and efficiently extracting a protein complex from cell lysate under conditions that preserve in vivo protein interactions.

Nevertheless, a common problem is the co-enrichment of proteins that associate non-specifically with the affinity-tagged complex (e.g., heat-shock or metabolic proteins). In order to attenuate non-specific interactions, researchers typically increase the stringency of the isolation conditions until the non-specific proteins are no longer present. However, it is difficult to determine whether the increased stringency also results in the loss of specific protein-protein interactions.

SUMMARY OF THE INVENTION

The present invention is method of determining whether or not associations between a given protein and other proteins in a cell are specific. The method comprises (a) providing a first sample of the cells in which the given protein contains a tag, (b) providing a second sample of the same cells, wherein the given protein and the other proteins are metabolically labeled, and wherein neither the given protein nor the other proteins are tagged, (c) mixing and lysing the first cell sample and the second cell sample to provide a mixture of proteins, (d) binding the tag of the given protein to a substrate, (e) isolating proteins associated with the tagged given protein bound to the substrate, whereby the associated proteins comprise: (i) proteins specifically associated with the tagged given protein, (ii) proteins non-specifically associated with the tagged given protein, or (iii) a combination thereof, (f) determining whether each associated protein is unlabeled or a mixture of labeled and unlabeled proteins, wherein if the associated protein is not labeled, then that protein was specifically associated in the cell with the tagged given protein.

Alternatively, the method comprises (a') providing a first sample of the cells, wherein neither the given protein nor the other proteins are tagged, (b') providing a second sample of the same cells in which the given protein contains a tag, wherein the given protein and the other proteins are metabolically labeled, (c') mixing and lysing the first cell sample and the second cell sample to provide a mixture of proteins, (d') binding the tag of the given protein to a substrate, (e') isolating proteins associated with the tagged given protein bound to the substrate, whereby the associated proteins comprise: (i) proteins specifically associated with the tagged given protein, (ii) proteins non-specifically associated with the tagged given protein, or (iii) a combination thereof, (f') determining whether each associated protein is labeled or a mixture of labeled and unlabeled proteins, wherein if the associated protein is labeled, then that protein was specifically associated in the cell with the tagged given protein.

In an illustrative embodiment, the present invention is a method of identifying whether a target protein (i.e., a given protein) specifically associates with a second protein in a cell. The method comprises (a) mixing and lysing a first cell sample and a second cell sample to provide a mixture of proteins comprising the target protein, wherein either the first cell sample or the second cell sample comprises metabolically labeled proteins, and wherein the target protein has a tag in either the first cell sample or the second cell sample, (b) isolating a protein associated with the target protein, and (c) determining whether the associated protein is unlabeled or a mixture of labeled and unlabeled proteins, thereby determining whether the associated protein specifically associates with the target protein in the cell. Note, only the target protein has a tag, i.e., the other proteins in the samples do not have a tag. In one embodiment, the first cell sample comprises metabolically labeled cells and the first cell sample comprises the target protein with the tag. In another embodiment, the second cell sample comprises metabolically labeled cells and the first cell sample comprises the target protein with the tag.

In another illustrative embodiment, the present invention is a kit, comprising a first cell sample and a container comprising a second cell sample, wherein the first cell sample and the second cell sample are of a same cell type, wherein the first cell sample comprises heavy-isotope labeled proteins, and wherein the ratio of cells in the first cell sample to cells in the second cell sample is known and is equal to or less than 100:1. Preferably, the container comprises the first cell sample and the second cell sample. In one example, the ratio of cells in the first cell sample to cells in the second cell sample is between 1.5:1 and 1:1.5. In one embodiment, the first cell sample or the second cell sample, further comprises a target protein with a tag. In another embodiment, the kit further comprises a container comprising a substrate with a cognate binding agent for the tag. In another embodiment, the kit further comprises a container comprising a substrate with a cognate binding agent for an antibody molecule.

One of the distinctions between the present invention vis-à-vis the prior art (e.g., Blagoev et al., *Nat. Biotechnol.* 2003 21:315-318; Schulze et al., *J. Biol. Chem.* 2004, 279:10756-10764) is that the samples are not perturbed with respect to one another, except that the target protein is tagged in one of the samples. Besides this tagging, the two samples are substantially identical. Heavy isotope labeling is not considered to be a perturbation. Additionally, the two samples are treated substantially the same.

After isolation of the affinity-tagged protein complex, specific protein interactions are identified by mass spectrometry as isotopically light, whilst non-specific interactions appear as a mixture of isotopically light and heavy. B) Examples of single-stage mass spectra of tryptic peptides from either specific (top) or non-specific (bottom) proteins. The 4 Da difference between the light and heavy peptides corresponds to d4-lysine labeling in the heavy cells.

FIG. 2. Immunoisolation of Pol2-PrA with I-DIRT analysis. A) Coomassie blue-stained gel of proteins co-enriching with Pol2-PrA from a mixture of isotopically light POL2-PRA and isotopically heavy wild-type cells. The lane gel was sliced as indicated, and the proteins were identified by mass spectrometry. B) Representative mass spectra of tryptic peptides from a specific interactor with Pol2-PrA (i.e., Dpb2) and a non-specific contaminant (i.e., Rps3). C) Results of I-DIRT analysis for all the proteins observed in the gel. The contaminants are revealed by virtue of their containing a 1:1 mixture of light and heavy isotopes; real interactors contain only light isotopes.

Figure 3:
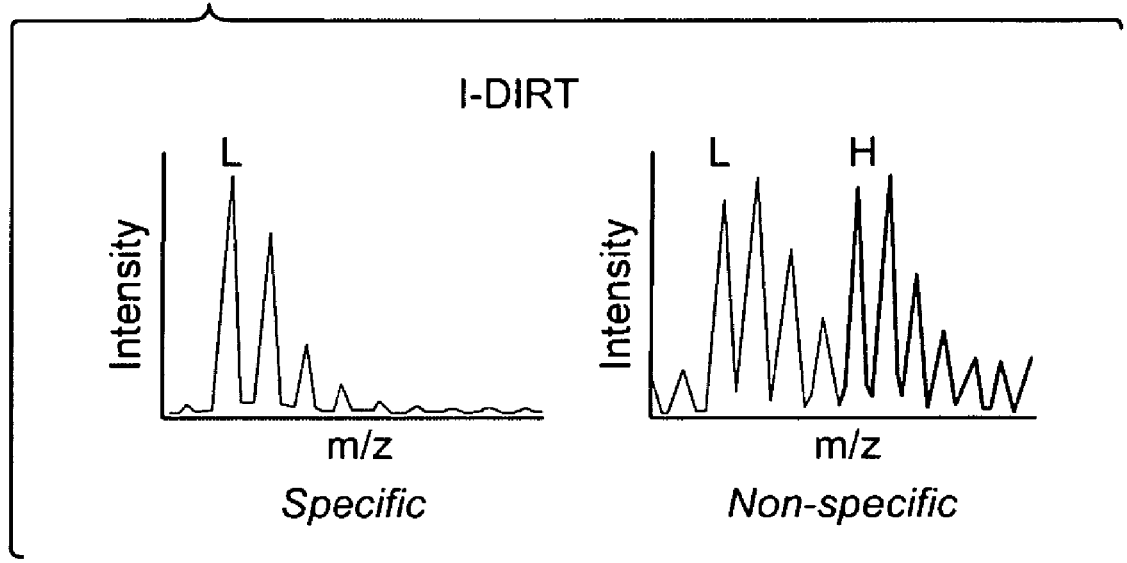

FIG. 3. Typical mass spectra for a specifically associated protein and a typical mass spectra for non-specifically associated protein.

DETAILED DESCRIPTION OF THE INVENTION

The present invention includes methods and kits used to distinguish contaminants from bona fide interactors in immunopurifications.

In one embodiment, the invention is a method of determining whether the association (i.e., interaction) between a given protein and other proteins in a cell are specific. A "given protein" is also known as a "target protein" in this specification.

A specific association between proteins is a specific protein-protein interaction that occurs in a cell. Specific associations between proteins are often involved in the regulatory mechanisms of a cell. Such mechanisms underlie, for example, intracellular communication, signal transduction, and the regulation of gene expression. Examples of non-specific protein associations include associations with heat-shock or metabolic proteins.

In this method, a first and a second sample of one or more cells are provided. Typically, the cells of the first sample are the same cell type as cells of the second sample. In illustrative embodiments, the one or more cells of the first sample are grown under identical conditions to the cells of the second sample before they are collected. The first and second cell samples can be in any ratio to each other by weight, e.g., within the range of 1:100 to 100:1, for example, within the range of 1:10 to 10:1, 1:5 to 5:1, 1 to 2, to 2:1, 1:1.5 to 1.5:1, or 1:1. In certain preferred embodiments, the ratio is 1:1. It will be understood that the cell ratio will be subject to statistical confidence limits of actual cell numbers. For example, the ratio can be based on 95% confidence limits on cell numbers.

In one embodiment of this method, the given protein in the first cell sample contains a tag to provide the tagged given protein. The tag may be any purification tag, or affinity tag, for which a cognate binding agent, such as an antibody is available. The given protein can also be a recombinant fusion protein comprising the tag.

An example of a preferred purification tag for which a cognate binding agent is readily available is the poly-histidine tag. Other useful purification tags include any epitope tag for which a cognate high affinity antibody is available or can be raised by well known methods.

Examples of common purification tags include glutathione S-transferase (GST), an epitope of GST, thioredoxin, or an epitope of thioredoxin and the commercially available FLAG epitope of influenza virus HA antigen. Other tags include streptavidin, maltose binding protein, Staphyloccocal protein A, Streptococcal Protein G, DHFR, Cellulose binding domains, calmodulin binding protein, a TAP tag, Green Fluorescent Protein (and its variants), Myc, FLU, T7, S-tag, beta-galactosidase, chiton binding domain, and chloramphenicol acetyltransferase. (Examples of these and other tags are found in Sambrook and Russel, 2001. Molecular Cloning, A Laboratory Manual. Third Edition. Cold Spring Harbor Laboratory, Cold Spring Harbor Press, NY.)

In one embodiment, the first cell sample is from a culture of cells grown in a standard medium, i.e., a medium comprising all twenty naturally occurring amino acids.

In this embodiment, neither the given protein nor the other proteins are tagged in the second sample of cells. Instead, the given protein and the other proteins are metabolically labeled in the second sample of cells.

Metabolic labeling can be performed by methods known in the art. A metabolic label can be, for example, a heavy (e.g., radioactive) isotope of one or more atoms of a biomolecule that is metabolized by cells. A heavy isotope can be heavy hydrogen, carbon, nitrogen, oxygen or sulfur. The biomolecule can be, for example, an amino acid, a nucleic acid, or a carbohydrate. The heavy isotopes have a mass difference from naturally occurring or a "light" isotope, that is detectable, for example by mass spectrometry. In illustrative embodiments, the heavy label is 4 or more Daltons, for example, between 4 and 10 Da heavier than a naturally occurring isotope, or than a light isotope. In certain examples, the metabolic labeling is performed using a heavy labeled amino acid, such as, but not limited to [13C6, 15N4]-L-Arginine (*Arg).

For example, a heavy isotope can be incorporated into the proteins by placing the sample of cells into a medium comprising a component with a heavy isotope. The component can be one or more heavy amino acids. Preferably, the heavy amino acids are heavy lysine and/or arginine. The component can also be a food source, e.g., glucose, sera or cell extracts. The component can also be ammonium sulfate. In this embodiment, the culture of cells that are harvested to provide the second cell sample is allowed to grow in the medium comprising the heavy isotope.

Next, the first cell sample and the second cell sample are mixed and lysed to provide a mixture of proteins. The mixing and lysing can take place in any order. Preferably, mixing is performed first. The mixing and lysing are performed by methods well known in the art.

Illustratively, the first cell sample and the second cell sample are separately collected and frozen in liquid nitrogen. Thereafter, equal amounts of the frozen samples are mixed together and the frozen cell mixture is disrupted by mechanical grinding. The frozen mixture is then thawed.

The mixture of proteins is exposed to a substrate comprising a cognate binding agent in order to bind the tag and thus the tagged given protein. Proteins associated with the tagged given protein also become bound to the substrate via the tagged given protein. The substrate in illustrative embodiments, is an affinity chromatography substrate, such as a bead, which can be packed in a column.

Methods for binding tags are well known in the art. For example, the cognate binding agent for the poly-histidine tag is a metal affinity column such as a nickel-affinity column. (Examples of other techniques are found in Sambrook and Russel, 2001. Molecular Cloning, A Laboratory Manual. Third Edition. Cold Spring Harbor Laboratory, Cold Spring Harbor Press, NY.)

The associated proteins which are bound to the substrate are then isolated. Preferably, the isolation is performed under non-stringent conditions, for example, on a gel or a column. Non-stringent conditions include, for example, lower than physiological salt concentrations and/or low levels of detergent, as would be known to a skilled artisan. Examples of non-stringent conditions include salt concentrations of less than 150 mM NaCl, e.g., 100 mM NaCl, and the absence of, or reduced levels of, detergents (e.g., tritionX, tween, NP-40). An example of a reduced level is less than 0.1% of detergent.

Although not a limitation of the invention, isolation using non-stringent conditions is an advantage of this invention. Isolations under non-stringent conditions permit a researcher to probe for more weakly bound or transient members of a protein complex. A protein complex is an arrangement of multiple folded protein molecules in a multi-subunit assembly. Examples of protein complexes include hemoglobin, DNA polymerase, and ion channels. The protein complexes can include proteins that are associated by non-covalent interactions.

The associated proteins comprise (i) one or more proteins specifically associated with the tagged given protein, and/or (ii) one or more proteins non-specifically associated with the tagged given protein, or (iii) a combination thereof.

A determination is made as to whether each associated protein is unlabeled or a mixture of labeled and unlabeled proteins. In this embodiment, if an associated protein is not labeled, then that protein is specifically associated in the cell (e.g., in vivo) with the given protein.

If the associated protein is a mixture of labeled and unlabeled proteins, then that protein became associated with the tagged given protein during or after cell lysis. In most cases, this association would be due to non-specific protein association.

If the ratio of the amount by weight of the first sample of cells to the second sample of cells is 1:1, then the mixture of the labeled and unlabeled proteins will contain approximately 50% of the unlabeled protein and approximately 50% of the labeled protein. A variation in the ratio will commensurately vary the percentage of labeled and unlabeled proteins.

Note, if there is fast exchange of a specific interactor in the lysate, then such an interactor may give the same signature as non-specific interactor. There are also intermediate cases, in which a specifically interacting protein exchanges with a soluble pool during immunoisolation. In such cases, the percent light (eq. 1) will lie somewhere between 100% and 50% depending on the equilibrium dissociation time constant; at 50% light a very rapidly exchanging protein would be indistinguishable from a contaminant. However, such occasional complications can be minimized by using short immunoisolation incubation times. (See Cristea et al., *Mol Cell Proteomics*. 2005 December; 4(12):1933-41.)

In an alternative embodiment of the invention, the method is as described above, except that instead of the given protein in the first cell sample being tagged, the given protein is tagged in the second cell sample. In other words, neither the given protein nor the other proteins are tagged in the first cell sample, and the given protein in the second cell sample contains a tag. As in the previous embodiment, the given protein and the other proteins are metabolically labeled in the second cell sample.

In this alternative embodiment, a determination is made as to whether the associated proteins are labeled or a mixture of labeled and unlabeled proteins. If an associated protein is labeled, then that protein is specifically associated with the given protein. If the associated protein is a mixture of labeled and unlabeled proteins, then that protein became associated with the tagged given protein during or after cell lysis. In most cases, this association would be due to non-specific protein association.

Determination as to whether the proteins are labeled, unlabeled, or are a mixture of labeled and unlabeled proteins is well known in the art. In one embodiment, proteins are separated, for example, using a gel, such as a polyacrylamide gel (e.g., SDS-PAGE).

In the embodiment in which heavy isotopes are used in labeling, the determination as to whether the separated proteins are labeled, unlabeled, or are a mixture of labeled and unlabeled proteins comprises deriving mass spectra data for the isolated proteins. Preferably, the proteins are digested prior to deriving the mass spectra. Preferably, the digestion is performed with trypsin. FIG. 3 shows typical mass spectra for a specifically associated protein and a typical mass spectra for non-specifically associated protein.

Preferably, there is at least a 1 dalton difference, more preferably at least a 4 dalton difference, between a non-specifically associated protein comprising the heavy isotope and the naturally-occurring counterpart of the non-specifically associated protein.

In the embodiment in which radioactive isotopes are used in labeling, the determination as to whether the separated proteins are labeled, unlabeled, or are a mixture of labeled and unlabeled proteins comprises determining the degree of radioactivity of the separated protein.

The present invention also includes test kits for determining whether an association between a given protein and other proteins in a cell is specific or non-specific. The test kits can comprise, for example, a growth medium comprising a metabolic label, such as a component with a heavy isotope as described above; and cells containing the given protein and the other proteins. The test kits can also comprise instructions describing the methods of the invention.

The cells can be any type of cells. For example, the cells can be vertebrate cells, yeast cells or bacterial cells. The vertebrate cells can be human cells or mouse cells. The human cells can be HeLa cells.

In another embodiment, the test kit can further comprise a medium without the component with the heavy isotope, i.e., a standard medium. In an another embodiment, the test kit can further comprise a tag suitable for tagging the given protein, as described above.

In yeast and bacteria, the tags can be introduced by genomic tagging, wherein the target gene (in its normal position on the chromosome) is replaced by the target gene coupled to additional DNA sequence that codes for the tag. In mammalian cells, the tagged gene is usually introduced on a plasmid.

In certain embodiments, the kits include a container of a labeled biomolecule, such as [13C6, 15N4]-L-Arginine (*Arg), or a container of a medium that includes a labeled biomolecule, such as [13C6, 15N4]-L-Arginine (*Arg). The kits can also include an affinity chromatography substrate.

In an illustrative embodiment, the present invention is a kit, comprising a first cell sample and a container comprising a second cell sample, wherein the first cell sample and the second cell sample are of a same cell type, wherein the first cell sample comprises heavy-isotope labeled proteins, and wherein the ratio of cells in the first cell sample to cells in the second cell sample is known and is equal to or less than 100:1. Preferably, the container comprises the first cell sample and the second cell sample. In one example, the ratio of cells in the first cell sample to cells in the second cell sample is between 1.5:1 and 1:1.5. In one embodiment, the first cell sample or the second cell sample, further comprises a target protein with a tag. In another embodiment, the kit further comprises a container comprising a substrate with a cognate binding agent for the tag. In another embodiment, the kit further comprises a container comprising a substrate with a cognate binding agent for an antibody molecule.

EXAMPLES

Yeast strains and growth conditions. *S. cerevisiae* strains are from the W303 background. One strain contained a Protein A (PrA) affinity tag at the C terminal coding sequence of the POL2 open reading frame. The POL2-PRA strain was grown in synthetic complete medium to mid-log phase at 30° C., harvested by centrifugation and frozen as pellets in liquid nitrogen (isotopically light cells). A wild-type strain was grown in synthetic medium lacking lysine, which was supplemented with 0.1 mg/mL DL-lysine-4,4,5,5-d4 2HCl (C/D/N Isotopes Inc.) to mid-log phase at 30° C., harvested by centrifugation and frozen as pellets in liquid nitrogen (isotopically heavy cells). Isotopically light and heavy cells were mixed 1:1 (by weight), disrupted with a Retsch MM301 mixer mill that was maintained at liquid nitrogen temperature, and stored at −80° C. A sample of isotopically light cells alone was also disrupted and stored at −80° C.

Immunoisolation and mass spectrometric identification of protein complexes. Immunoisolation of Pol2-PrA and associated proteins was performed as described except that the stringency of the purification buffer was lowered by decreasing the NaCl concentration to 100 mM rather than 300 mM. These less stringent conditions were used to deliberately increase the level of non-specific associations with the Pol2-PrA-containing complexes. One gram of the mixture of lysed isotopically light (POL2-PRA) and heavy (wild-type) cells were used for the immunoisolation. As a control, an immunoisolation was performed on 0.5 g of lysate from isotopically light POL2-PRA cells alone.

Protein complexes containing Pol2-PrA were resolved by SDS-PAGE on 4-20% polyacrylamide gels (Invitrogen) and visualized by Coomassie blue-staining. The entire gel lane (5.2 cm long) was sliced into 17 sections and proteins in each gel slice were identified by MALDI-mass spectrometry. Briefly, a mass spectrum of tryptic peptides derived from each gel slice was obtained with an in-house modified MALDI-QqTOF mass spectrometer (Sciex Centaur, Concord, ON). All m/z values with a signal-to-noise of >2 were subjected to MALDI-MS/MS analysis with an in-house modified MALDI-ion trap mass spectrometer (Finnigan LCQ, ThermoElectron Corp., San Jose, Calif.). Single-stage and multistage mass spectrometric data was used for protein identification with the program XProteo (www.xproteo.com).

Measurement of isotopic ratios. A list of tryptic peptides containing at least one lysine residue was obtained for each of the proteins identified from the mass spectrometric data (see above). For each of these lysine-containing peptides, the program M-over-Z was used to visualize a range of the single-stage MALDI-mass spectrum that was large enough to display the isotopically light lysine-containing peptide as well as the heavy version of the peptide. The heavy version of the peptide will be shifted from the light version by 4 Da increments per d4-lysine. Using the M-over-Z program, monoisotopic peak areas was obtained for the isotopically light ($A_L$) and heavy ($A_H$) peptides. Peak areas were corrected by background subtraction. Since the natural isotopic distribution of the light peptide may overlap with the monoisotopic peak of the heavy peptide, $A_H$ was further corrected with the theoretical isotopic overlap determined from the program Isotopident (http://haven.isb-sib.ch/tools/isotopident/htdocs/). Then the corrected $A_L$ and $A_H$ values were used to determine the percent of the peptide that was isotopically light. These calculations are shown in Equation 1:

$$\% \text{ light} = \frac{(A_L - A_B)}{(A_L - A_B) + ([A_H - A_B] - [I_O \times \{A_L - A_B\}])} \times 100 \quad \text{Eq. 1}$$

The additional variables in Equation 1 are as follows: $A_B$=background peak area; $I_O$=theoretical fraction of isotopic overlap of the natural isotope peak from the light peptide with the monoisotopic peak from the heavy peptide. In cases where more than one lysine-containing peptide was identified for a given protein, the average of the % light measurements together with the standard deviation is reported.

Results and Discussion

Figure 1B:
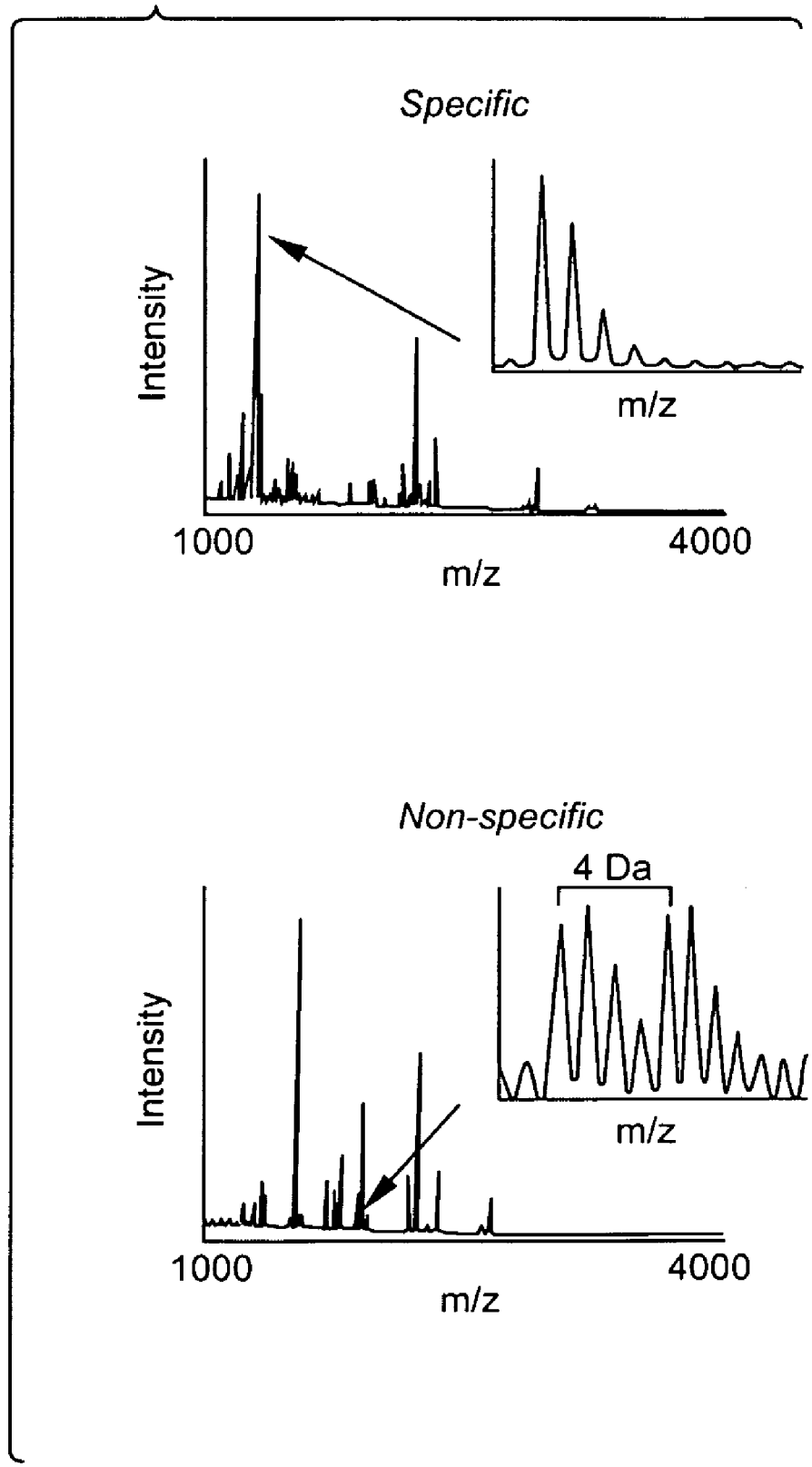
FIG. 1. I-DIRT procedure for determining specific members of a protein complex. A) Cells containing an affinity-tagged protein are grown in light isotopic medium, while wild-type cells are grown in heavy isotopic medium (d4-lysine). Equal quantities of these two cell preparations are mixed and the affinity-tagged protein complex is isolated.

The I-DIRT technique. The I-DIRT (Isotopic Differentiation of Interactions as Random or Targeted) technique is outlined in FIG. 1A. Cells containing an affinity-tagged protein are grown in light isotopic medium, while wild-type cells are grown in heavy isotopic medium (here d4-lysine). Cells from the isotopically light and heavy cultures are mixed at a 1:1 ratio by cell weight. The heavy:light cell mixture is thoroughly blended and lysed under cryogenic conditions. The isotopically light affinity-tagged protein is immunoisolated on affinity resin. Co-enriching with the affinity-tagged protein will be both specifically and non-specifically interacting proteins. The specifically interacting proteins, which form their association with the tagged protein prior to cell lysis, are exclusively light labeled. In contrast, the non-specific proteins, which form their association with the tagged protein after thawing of the lysed mixture of light and heavy cells, are both isotopically heavy and light labeled. After isolation of the affinity-tagged protein complex and trypsin digestion of the co-enriching proteins, specifically interacting proteins are identified by mass spectrometry as isotopically light, whilst non-specifically interacting proteins appear as a mixture of isotopically light and heavy (FIG. 1B).

Preparation of samples for I-DIRT. The I-DIRT procedure requires an isotopically light and heavy preparation of cells (FIG. 1A). When incorporating a heavy isotope into cellular proteins, one should choose an isotopically heavy metabolite to produce a mass shift that will be readily resolved from a light peptide by mass spectrometric analysis. For example, choosing a heavy metabolite that yields a 1 Da mass difference between a heavy and light peptide will produce mass spectra that will be difficult to interpret due to the natural isotopic distribution of the light peptide. Thus, d4-lysine was used, which will produce a 4 Da difference between light and heavy single-lysine containing peptides (or an 8 Da difference for peptides containing two lysines). This 4 Da shift is readily distinguished by our MALDI-QqTOF mass spectrometer (FIG. 1B). To produce an isotopically heavy yeast sample, d4-lysine was provided as the only source of lysine to wild-type *S. cerevisiae*. Wild-type yeast grown in the presence of d4-lysine only incorporated isotopically heavy lysine into polypeptides (AJT and BTC, unpublished observation). A sufficient quantity of the heavy-labeled reference yeast (2 liters) was cultured to allow for multiple I-DIRT experiments with a variety of tagged strains. Cells isolated by centrifugation were frozen as small pellets in liquid nitrogen, and stored at −80° C. until needed for the I-DIRT procedure.

A culture of yeast containing a C-terminal PrA tag on the POL2 gene (POL2-PRA) was grown in synthetic complete medium. These isotopically light cells, incorporating natural lysine into its polypeptides, were collected by centrifugation, frozen as small pellets in liquid nitrogen and stored at −80° C.

To prepare a cellular lysate for immunoisolation with I-DIRT analysis, wild-type (heavy) and affinity-tagged (light) frozen cell pellets were mixed at a 1:1 ratio (by weight). This mixture of light and heavy cells was cryogenically lysed in a mixer mill maintained at liquid nitrogen temperature (Retsch MM301). Care was taken to ensure that the cells did not thaw at any stage of the grinding process. The resulting frozen mixture of lysed heavy and light cells can be stored at −80° C., and utilized in aliquots for multiple immunoisolations with I-DIRT analysis. A control lysate was also prepared from isotopically light POL2-PRA cells alone.

Immunoisolation of Pol2-PrA with I-DIRT analysis. To test the I-DIRT method, the DNA polymerase epsilon (pol $\epsilon$) catalytic subunit, Pol2, which was genomically-tagged with PrA, was immunoisolated. This polymerase has been extensively studied and found to be a stable complex of four proteins: Pol2, Dpb2, Dpb3, and Dpb4. Immunoisolation of Pol2-PrA under stringent conditions (i.e., 300 mM NaCl) yields the three other members of pol $\epsilon$, but also co-enriched lower levels of potentially non-specific proteins (including ribosomal and heat shock proteins). Here, the stringency (100 mM NaCl) of the Pol2-PrA immunoisolation was deliberately decreased to increase the level of potential non-specific proteins and assayed with I-DIRT for specific protein interactions (FIG. 2).

Figure 2A:
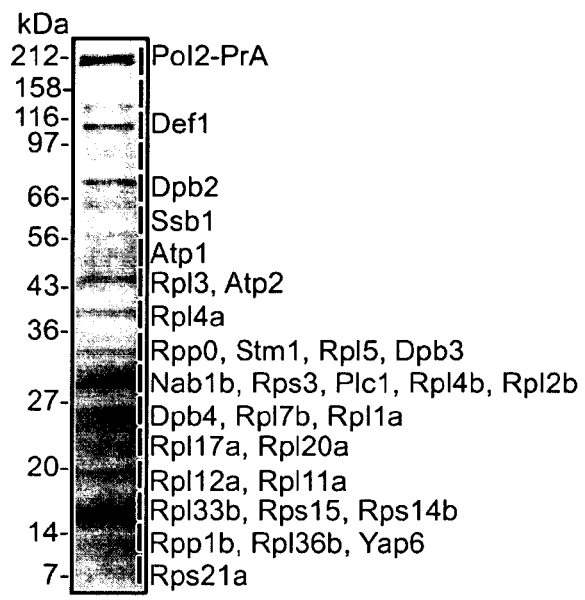
Figure 2B:
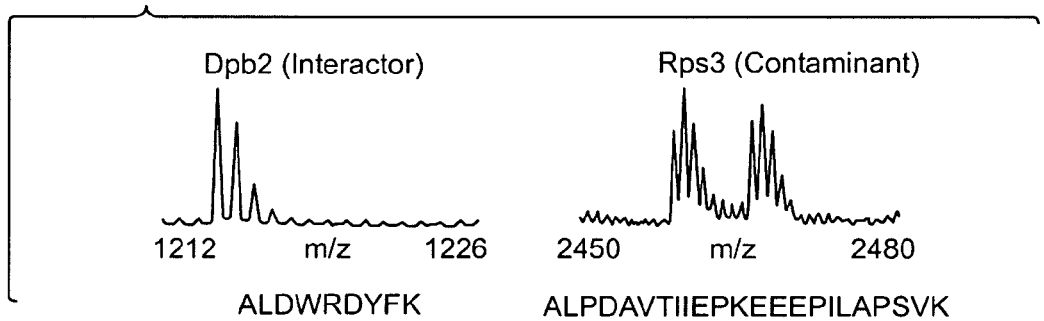

Two types of Pol2-PrA immunoisolations were performed: (1) POL2-PRA (light) mixed with wild-type (heavy) cells and (2) POL2-PRA (light) cells alone as a control. The proteins that co-purified with Pol2-PrA were resolved by SDSPAGE and visualized by Coomassie blue-staining (FIG. 2A). The entire gel lane was sliced from top to bottom and proteins in each gel slice were digested with trypsin. A mass spectrum of tryptic peptides derived from each gel slice was obtained by MALDI-QqTOF mass spectrometry (FIG. 2B). All ion peaks with a signal-to-noise of >2 were subjected to MALDI-ion trap $MS^2$. The resulting MS and $MS^2$ data was used for protein identification.

A list of tryptic peptides containing at least one lysine residue was obtained for each of the proteins identified by mass spectrometry. For each of these lysine-containing peptides, the program M-over-Z was used to visualize a range of the single-stage mass spectrum that was large enough to display the h4-lysine-containing peptide as well as the corresponding d4-lysine-containing peptide, should it be present (FIG. 2B). For each gel slice, the mass spectra obtained in the heavy:light and that from the light only immunoisolations was compared. This comparison allowed to determine whether there were any light peptide peaks that could potentially interfere with the observation of a given putative heavy peptide component.

In the mass spectrum from the heavy:light immunoisolation, the heavy peptide is shifted by 4 Da increments per d4-lysine. Monoisotopic peak areas for the isotopically light and heavy peptides was obtained, and the fraction of the peptide that was isotopically light was determined (Equation 1). If more than one lysine-containing peptide was identified from a given protein, then the average of the multiple measurements of the light fraction was reported together with the standard deviation of these measurements (FIG. 2C).

Figure 2C:
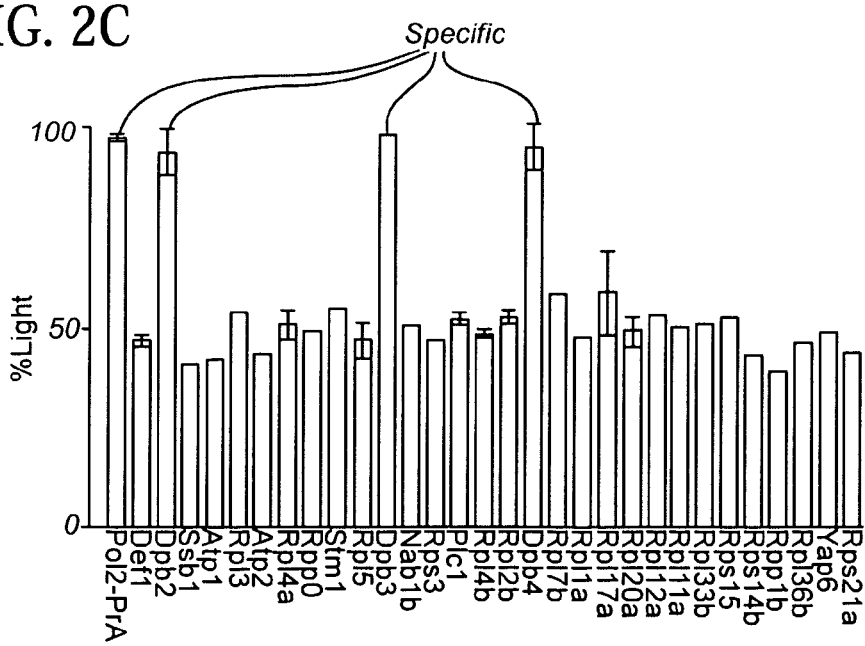

The results of the I-DIRT analysis of the Pol2-PrA immunoisolation are shown in FIG. 2C. If the percentage light for a protein approaches 100%, then that protein has maintained its interaction with Pol2-PrA from the isotopically light cells and is therefore a specific interaction. If the percentage light for a protein is approximately 50%, then that protein has non-specifically associated with the Pol2-PrA complex during the immunoisolation procedure (because there is a 50% chance that either an isotopically light or heavy version of the protein in the mixed tagged and reference cell lysate will non-specifically bind). As predicted, specific interactions for the four known components of pol $\epsilon$ (Pol2, Dpb2, Dpb3, Dpb4) was observed, while the remaining proteins were found to associate non-specifically. Thus, all members of the pol c protein complex was identified and distinguished from non-specific proteins under non-stringent conditions.

The I-DIRT technique was also utilized on the well-defined Nup84 subcomplex of the nuclear pore complex. As with the pol C complex, non-specific proteins were distinguished from the published complex members (data not shown), thereby validating the technique on a distinct protein complex.

The invention claimed is:

1. A method of determining whether or not associations between a given protein and other proteins in a cell are specific, the method comprising:
   (a) providing a first sample of the cells in which the given protein contains a tag,
   (b) providing a second sample of the same cells, wherein the given protein and the other proteins are metabolically labeled, and wherein neither the given protein nor the other proteins are tagged,
   (c) mixing and lysing the first cell sample and the second cell sample to provide a mixture of proteins,
   (d) binding the tag of the given protein to a substrate,
   (e) isolating proteins associated with the tagged given protein bound to the substrate, whereby the associated proteins comprise:
      (i) proteins specifically associated with the tagged given protein,
      (ii) proteins non-specifically associated with the tagged given protein, or
      (iii) a combination thereof,
   (f) determining whether each associated protein is unlabeled or a mixture of labeled and unlabeled proteins, wherein if the associated protein is not labeled, then that protein was specifically associated in the cell with the tagged given protein.

2. The method of claim 1 wherein if the associated protein is a mixture of labeled and unlabeled proteins, then that protein became associated with the tagged protein during or after cell lysis.

3. The method of claim 1 wherein the tagged protein is a member of a protein complex.

4. The method of claim 1 wherein the isolation in step (e) is performed at non-stringent conditions.

5. The method of claim 1 wherein the metabolic label is a heavy isotope.

6. The method of claim 1 wherein the metabolic label is a radioactive isotope.

7. The method of claim 6 wherein the heavy isotope is heavy hydrogen, carbon, nitrogen, oxygen and/or sulfur.

8. The method of claim 5 wherein determining whether the associated protein is labeled, unlabeled, or a mixture of labeled and unlabeled proteins comprises deriving mass spectra data for the isolated proteins.

9. The method of claim 8 wherein the ratio of the number of cells in the first sample to the number of cells in the second sample is in the range of 1:100 to 100:1.

10. The method of claim 9 wherein the ratio of the number of cells in the first sample to the number of cells in the second sample is approximately 1:1.

11. The method of claim 8 further comprising digesting the isolated proteins before deriving mass spectra data.

12. The method of claim 8 wherein there is between a 1 and 4 dalton difference between a non-specifically associated protein comprising the heavy isotope and the naturally-occurring counterpart of the non-specifically associated protein.

13. The method of claim 8 wherein there is at least a 4 dalton difference between a non-specifically associated protein comprising the heavy isotope and the naturally-occurring counterpart of the non-specifically associated protein.

14. The method of claim 6 wherein the heavy isotope is incorporated into the proteins by placing the first or second sample of cells in a medium comprising a component with a heavy isotope, wherein the cells produce proteins incorporating the component.

15. The method of claim 14, wherein the component is one or more heavy amino acids.

16. The method of claim 15 wherein the heavy amino acid is heavy lysine and/or arginine.

17. The method of claim 14 wherein the component is a food source.

18. The method of claim 14 wherein the component is glucose.

19. The method of claim 14 wherein the component is sera or cell extracts.

20. The method of claim 14 wherein the component is ammonium sulfate.

21. The method of claim 1 wherein the proteins are tagged with glutathione-S-transferase, polyhistidine, polyarginine, the FLAG epitope, streptavidin, maltose binding protein, thioredoxin, intein, Staphyloccocal protein A, Streptococcal Protein G, DHFR, Cellulose binding domains, calmodulin binding protein, a TAP tag, Green Fluorescent Protein, Myc, FLU, T7, S-tag, beta-galactosidase, chiton binding domain, and/or chloramphenicol acetyltransferase.

22. The method of claim 1 wherein the tag is an epitope of any protein that is recognized by a specific cognate partner.

23. The method of claim 22 wherein the cognate partner is an antibody.

24. The method of claim 6 wherein determining whether the associated protein is labeled, unlabeled, or a mixture of labeled and unlabeled proteins comprises determining the degree of the radioactivity of the isolated proteins.

25. A method of identifying whether a target protein specifically associates with a second protein in a cell, the method comprising:
(a) mixing and lysing a first cell sample and a second cell sample of the same cell type to provide a mixture of proteins comprising the target protein, wherein either the first cell sample or the second cell sample comprises metabolically labeled proteins, and wherein the target protein has a tag in either the first cell sample or the second cell sample,
(b) isolating a protein associated with the target protein, and
(c) determining whether the associated protein is unlabeled or a mixture of labeled and unlabeled proteins, thereby determining whether the associated protein specifically associates with the target protein in the cell.

26. The method of claim 25, wherein the first cell sample comprises metabolically labeled cells and wherein the first cell sample comprises the target protein with the tag.

27. The method of claim 25, wherein the second cell sample comprises metabolically labeled cells and wherein the first cell sample comprises the target protein with the tag.

28. The method of claim 25, wherein the target protein is a recombinant fusion protein comprising the tag.

29. The method of claim 28, wherein the tag is a polyhistidine tag.

30. The method of claim 25, wherein the isolating comprises binding the target protein with the tag to a cognate binding agent with a substrate.

* * * * *